United States Patent [19]

van der Knaap

[11] Plant 4,588

[45] Aug. 19, 1980

[54] CHRYSANTHEMUM NAMED EARLY YELLOW

[75] Inventor: J. C. M. van der Knaap, De Lier, Netherlands

[73] Assignee: Pan-American Plant Company, West Chicago, Ill.

[21] Appl. No.: 13,302

[22] Filed: Feb. 21, 1979

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Chas. W. Rummler

[57] ABSTRACT

A new variety of light yellow chrysanthemum for greenhouse culture distinguished by its relatively short response, its rapid growth and the intense color of its blooms, its uniform year around flowering response, and its usefulness both for spray pot plant culture and as a spray plant for cut flower production.

4 Drawing Figures

BACKGROUND OF THE NEW PLANT

This new chrysanthemum plant was originated by me in 1972 as a seedling resulting from the cross of the unpatented variety "Dramatic" and an unknown pollen parent, the crossing having been made in the course of breeding efforts carried on by me at De Lier, Holland, for the development of improved chrysanthemum varieties. Because of its intense yellow color, rapid growth, and very strong stems, this plant was selected for propagation, and test, which was done under my direction at De Lier, Holland, by means of cuttings from the original plant, and propagation of the new plant through successive generations by vegetative cuttings has shown that its distinctive characteristics hold true and appear to be firmly fixed. Commercial scale propagation of this new chrysanthemum variety is now being done by vegetative cuttings at West Chicago, Ill., and at Cortez, Fla., U.S.A.

DESCRIPTION OF THE DRAWINGS

My new variety of chrysanthemum is illustrated by the accompanying drawings, of which the first sheet is a photographic rendition of a potted plant in full bloom, the photographic print having been hand painted to show the true color of the blooms, and the second sheet is a print of a mechanical reproduction of typical leaves of the new plant.

DESCRIPTION OF THE NEW PLANT

The following is a detailed description of my new chrysanthemum variety based upon observations made at West Chicago, Ill., U.S.A., in the Spring of 1978, the color designations being accorded to The R.H.S. Colour Chart published by The Royal Horticultural Society of London, England.

THE PLANT

Origin: Seedling.

Parentage:

*Seed parent.*—Dramatic (unpatented).

*Pollen parent.*—Unknown.

Classification:

*Botanic.*—*Chrysanthemum morifolium.*

*Commercial.*—Greenhouse pot plant and plant for cut flower production.

Form: Perennial herbaceous bush.

Height:

*As a pot plant.*—About 32 to 41 cm.

*As a plant for cut flower production.*—90 to 110 cm.

Growth: Terminal. Vigorous, sturdy and upright with very good strength.

Branching: Normal, under natural conditions.

Foliage: Abundant, with 4 leaves per 10 cm. of stem.

*Leaf size.*—Length — about 8.5 to 17.8 cm. Width —about 4.3 to 10.3 cm.

*Shape.*—Lobed, lanceolate and slightly serrated.

*Surface texture.*—Canescent.

*Venation.*—Pinnate.

*Color.*—Upper side — 147A. Under side — 147B.

*Petioles.*—About 2.1 to 4.2 cm. in length.

THE BUD

Form: Globular.

Size:

*Diameter.*—About 1.1 to 1.3 cm.

*Depth.*—About 0.7 to 0.8 cm.

Opening rate: Bud opens slowly.

Color:

*When phyllaries first divide.*—2C.

*When florets begin to unfurl.*—12A.

Phyllaries: The outer side of the receptacle bears many distinct involucral bracts which are spear-shaped and upstanding.

*Color.*—Inside — 137A. Outside — 137B.

*Surface texture.*—Canescent.

Peduncle: Erect and strong.

*Length.*—5 to 13 cm.

*Surface texture.*—Pubescent.

THE FLOWER

Response: 7 to 8 weeks.

Recommended flowering: Year around.

Natural flowering season: October 23 to October 30.

Blooms:

*Flower type.*—Composite and single.

*Size.*—Medium. Diameter — about 9.5 to 10.5 cm. Depth — About 2.5 to 3.0 cm.

*Borne.*—A single head comprising many florets borne on a receptacle.

*Shape.*—Cup-shaped when the bloom first opens with the ray florets tending to approach a common plane as the bloom matures.

Florets:

*Number.*—Numerous.

*Form.*—Linear with obtuse apex.

*Character.*—Firm.

*Appearance.*—Very slight shine.

*Color.*—Ray florets: Upper side — 6A. Reverse side — 6C.

*Tonality at a distance of 6 feet.*—6A.

Peduncle:

*Strength.*—Sturdy and upright.

*Length.*—About 5 to 13 cm.

*Color.*—147B.

Persistence: Florets hang on and dry.

Discoloration after full bloom: A very slight fade.

Fragrance: Typical chrysanthemum.

Lasting quality:

*On the plant.*—About 4 weeks.

*As a cut flower.*—About 3 weeks.

REPRODUCTIVE ORGANS

Stamens:

*Anthers.*—Number — 5. Arrangement — syngenesious.

*Filaments.*—Length: About 2 to 4.5 mm. Color: Light yellow.

*Pollen.*—Color — yellow.

Pistils:

*Number.*—One to each ray and disc floret.

*Styles.*—Length — about 4 to 6 mm.

*Stigma.*—Color — yellow.

Ovaries: Interior and bicarpellate.

The particular distinctions of this new variety of chrysanthemum reside in the intense yellow color of its single flower form with the blooms averaging about 10 cm. in diameter and with light to moderate pollen production. This new plant has a photoperiodic response of about 7 to 8 weeks with flowering capability the year around. The foliage is glossy and dark green in color and the blooms are numerous, which makes the plant useful both as a spray pot plant and as a plant for the production of cut flowers.

I claim:

1. A new and distinct variety of chrysanthemum plant, substantially as herein shown and described, characterized by its vigorous and rapid growth habit, its year-around uniform flowering response, and its early 7 to 8 week photoperiodic response.

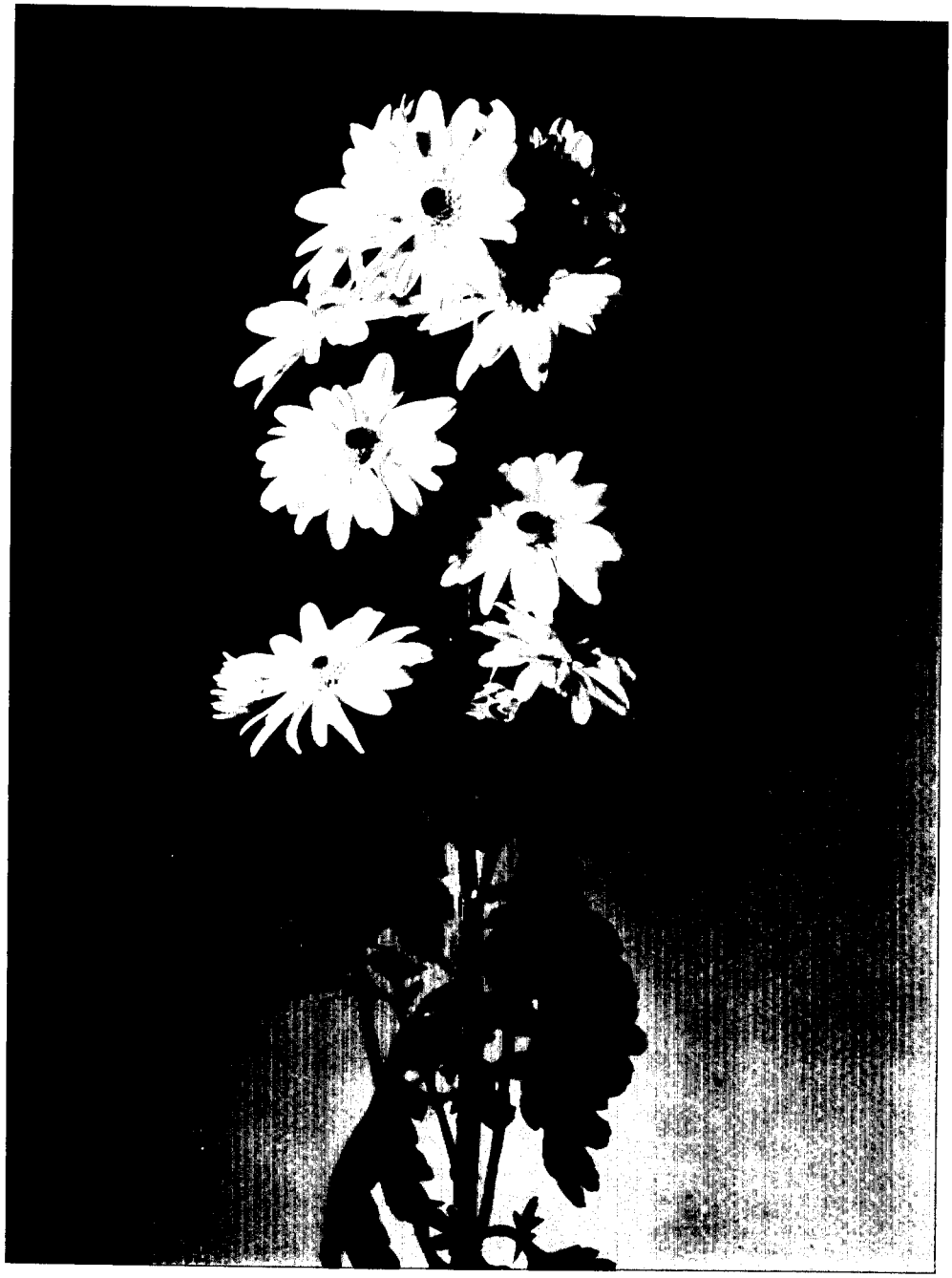

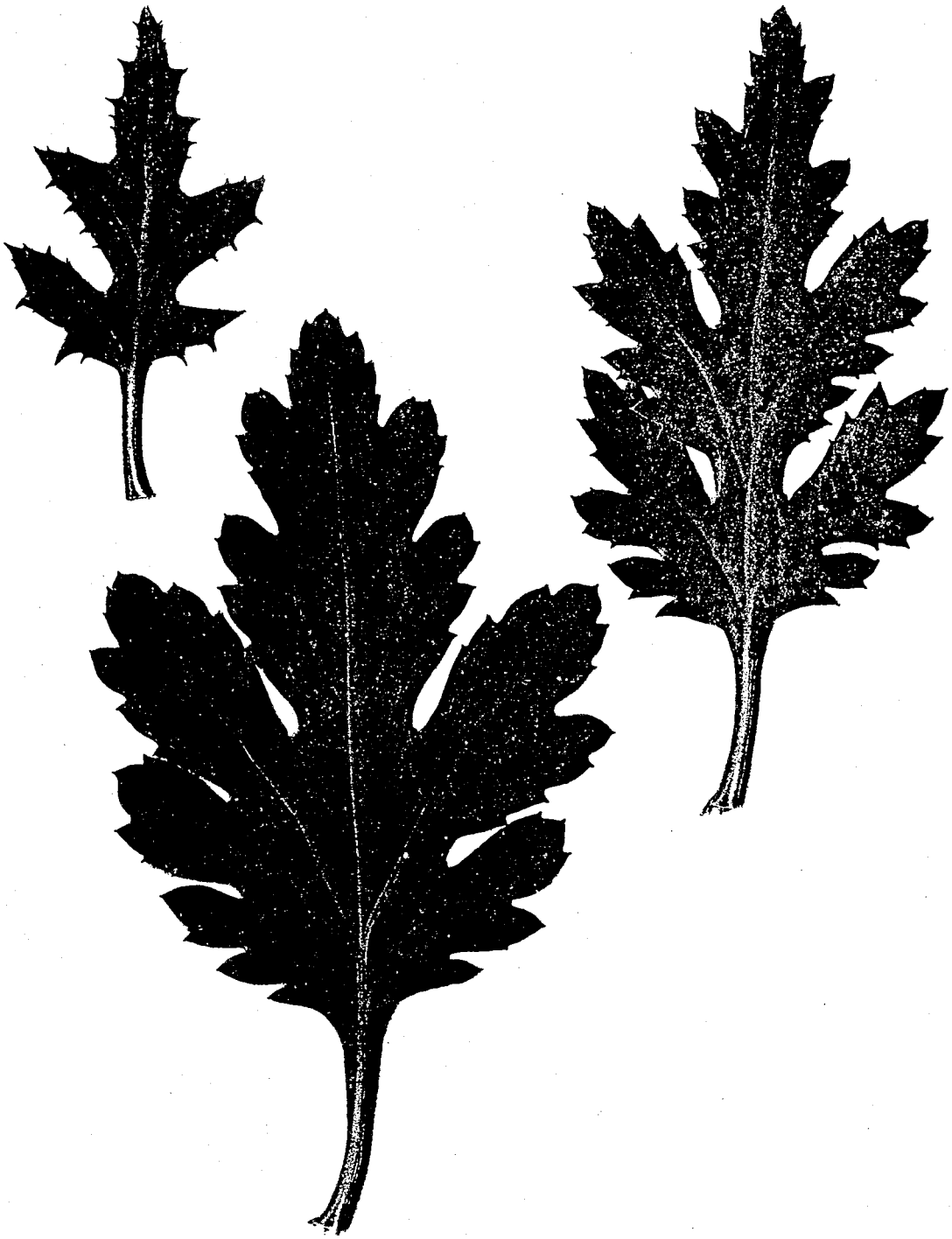

* * * * *